(12) United States Patent
Huang et al.

(10) Patent No.: US 6,200,786 B1
(45) Date of Patent: Mar. 13, 2001

(54) PROCESS FOR THE PREPARATION OF NOOTKATONE BY LACCASE CATALYSIS

(75) Inventors: Rongmin Huang, West Chester; Philip A. Christenson, Loveland, both of OH (US); Ivica M. Labuda, Mahwah, NJ (US)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 09/391,785

(22) Filed: Sep. 8, 1999

(51) Int. Cl.$^7$ .............................. C12P 7/00; C07C 45/00; C07C 35/22

(52) U.S. Cl. ................ 435/132; 435/254.1; 568/342; 568/346; 568/354; 568/356; 568/361

(58) Field of Search ...................... 568/342, 346, 568/354, 356, 361; 435/132, 254.1

(56) References Cited

U.S. PATENT DOCUMENTS

| | | | |
|---|---|---|---|
| 4,798,799 | 1/1989 | Farbood et al. | 435/254 |
| 5,847,226 | 12/1998 | Muller et al. | 568/346 |

FOREIGN PATENT DOCUMENTS

| | | |
|---|---|---|
| 2181025 | 7/1996 | (CA) . |
| 59-31728 | 8/1982 | (JP) . |
| 6-303967 | 4/1993 | (JP) . |

OTHER PUBLICATIONS del Rio et al., *Accumulation of the sesquiterpenes nootkatone and valencene by callus cultures of Citrus paradisi, Citrus limonia and Citrus aurantium*, Plant Cell Reports, vol. 10, p. 410–413 (1991).
Potthast et al., *A novel method for the converison of benzyl alcohols to benzaldehydes by laccase–catalyzed oxidation*, Journal of Molecular Catalysis A: Chemical 108 (1996), pp. 5–9.
Sutherland et al., *Biotransformation of isoquinoline, phenanthridine, phthalazine, quinazoline, and quinoxalne by Streptomyces viridosporus*, Appl. Microbiol. Biotechnol, vol. 49, p. 445–449 (1998).
Hunter et al., *Conversion of Valencene to Nootkatone*, p. 876–878 (1965).
Johannes et al., *Degradation of anthracene by laccase of Trametes versicolor in the prsence of differetn mediator compounds*, Appl. Microbiol. Biotechnol. vol. 46, p. 313–317 (1996).
Miyakoshi et al., *Dehydrogenative Polymerization of Isoeugenol and Coniferyl Alcohol by Laccases*, ISWPC, p. 103–104 (1997).
Jonsson et al., *Detoxification of wood hydrolysates with laccase and peroxidase from the white–rot fungus Trametes versicolor*, Appl Microbiol Biotechnol, 49, p. 691–697 (1998).

Willershausen et al., *Enzymatic transformation of valencene to nootkatone*, Chemiker Zeitung 115, p. 358–360 (1991). Partial translation.
Bailey et al., *Enzymic Oxidation of o–Aminophenols*, Chemical Communictions p. 408–409 (1967).
Kristopaitis et al., *Fungal peroxidase– and laccase–catalyzed oxidation of 1–hydroxybenzotriazole*, ISSN 1392–0146. Biologija. No. 4, p. 33–38 (1986).
Shaw et al., *Importance of Nootkatone to the Aroma of Grapefruit Oil and the Flavor of Grapefruit Juice*, J. Agric. Food Chem. 29, p. 677–679 (1981).
Sugumaran et al., *Laccase– and Not Tyrosinase—Is the Enzyme Responsible for Quinone Methide Production from 2,6–Dimethoxy–4–allyl Phenol*, Archives of Biochemistry and Biophysics, vol. 353, No. 2, p. 207–212, May (1988).
Eggert, *Laccase–catalyzed formation of cinnabarinic acid is responisble for antibacterial activity of Pycnoporus cinnabarinus*, Microbiol. Res. 152, p. 315–318 (1997).
Garzillo et al., *Laccase from the white–rot fungus Trametes trogii*, Appl. Microbiol Biotechnol, vol. 49, p. 545–551 (1998).
Xu et al., *Mediator–assisted selective oxidation of lignin model compounds by laccase from Botrytic cinerea*, Biotechnology Letters, 19, No. 10, p. 957–960 (1997).
Johannes et al., *Oxidation of acenaphthene and acenaphthylene by laccase of Trametes versicolor in a laccase mediator system*, Journal of Biotechnology, 61, p. 151–156 (1998).
Collins et al., *Oxidation of Anthracene and Benzo[a]pyrene by Laccases from Trametes versicolor*, Appl. Environ. Microbiol., 61, 12, p. 4563–4567 Dec. (1996).
Malovik et al., *Oxidation of Lignins and Their Components by Oxygen in the Presence of Laccase from Polyporus verwsicolor, Lignin Detection by an Enzyme Electrode*, Collection Czechoslovak Chem. Commun., vol. 49, p. 1390–1394 (1984).
Bourbonnais et al., *Oxidation of non–phenolic substrates, An expanded role for laccase in lignin biodegradation*, Federation of European Biochemical Societies, vol. 267, No. 1, p. 99–102 (1990).
Bohmer et al., *Oxidation of Phenanthrene by a Fungal Laccase in the Presence of 1–Hydroxybenzotriazole and Unsaturated Lipids*, Biochemical and Biophysical Research Communications 244, 233–238 (1998).
Majcherczyk et al., *Oxidation of polycyclic aromatic hydrocarbons (PAH) by laccase of Trametes versicolor*, Enzyme Microb. Technol., vol. 22, p. 335–341 Apr. (1988).

(List continued on next page.)

*Primary Examiner*—Sreeni Padmanabhan
(74) *Attorney, Agent, or Firm*—Wood, Herron & Evans, LLP (57) ABSTRACT

A method of producing nootkatone by laccase catalyzed oxidation of valencene. Valencene and a composition having laccase activity are reacted in the presence of an oxygen source, at a valencene concentration greater than 0.1%, to form valencene hydroperoxide. Optionally, a mediator and/or a solvent at a concentration that maintains laccase activity may also be included. The valencene hydroperoxide is degraded to form nootkatone, and nootkatone is then recovered. The method produces nootkatone in commercially viable yields.

38 Claims, 6 Drawing Sheets

OTHER PUBLICATIONS

Faure et al., Phenolic Derivatives Related to Lignin Metabolism as Substrates for Azospirillum Laccase Activity, Phytochemistry, vol. 42, No. 2, p. 357–359 (1996).

Slomczynski et al., Production and Characterization of Laccase from *Botrytis cinerea* 61–34, Applied and Environmental Microbiology, vol. 61, No. 3, p. 907–912 (1995).

Drawert et al., Regioselective biotransformation of valencene in cell suspension cultures of Citrus sp., Plant Cell Reports, vol. 3, p. 37–40 (1984).

Bombarda et al., Sesquiterpenic Epoxides and Alcohols Derived from Hydrocarbons of Vetiver Essential Oil, J. Agric. Food Chem. 44, p. 217–222 (1996).

Fritz–Langhals et al., Synthesis or aromatic aldehydes by laccase–mediator assisted oxidation, Tetrahedron Letters, 39, p. 5955–5956 (1996).

Wilson et al., Synthesis of Nootkatone from Valencene, J. Agric. Food Chem, vol. 26, No. 6, p. 1430–1432 (1978).

Amann, The Lignozym® Process—coming Closer to the Mill, ISWPC p. F4–1 to 5 (1997).

PROCESS FOR THE PREPARATION OF NOOTKATONE BY LACCASE CATALYSIS

FIELD OF THE INVENTION

The invention is directed generally to production of natural flavors, and specifically to production of natural flavors by laccase catalysis.

BACKGROUND OF THE INVENTION

The food and beverage industries, as well as other industries such as the cosmetic industry and the health care industry, routinely use flavors to enhance their products' appeal. Natural flavors are especially desired by consumers for reasons of health, fitness, safety, aesthetics, etc. Worldwide consumer demand for natural flavors thus continues to increase. Natural flavors or natural flavorings have been defined at 21 C.F.R. §101.22 as the essential oil, oleoresin, essence or extractive, protein hydrolysate, distillate, or any products of roasting, heating or enzymolysis which contains the flavoring constituents derived from a spice, fruit or fruit juice, vegetable or vegetable juice, edible yeast, herb, bark, bud, root, leaf or similar plant material, meat, seafood, poultry, eggs, dairy products or fermentation products thereof, whose significant function in food is flavoring rather than nutrition.

One such flavor is nootkatone (4,4a,5,6,7,8-hexahydro-6-isopropenyl-4,4a-dimethyl-2(3II)-naphtalenone). Nootkatone is an important flavor constituent of grapefruit and is used commercially to flavor soft drinks and other beverages, as well as being used in perfumery. The conventional method for nootkatone preparation is by oxidation of valencene. However, nootkatone prepared by standard chemical oxidation methods cannot be considered a natural flavorant and thus has less commercial desirability. Additionally, the starting material valencene is expensive and thus methods that consume valencene are less commercially acceptable. Because of these drawbacks, there is still a need for commercially feasible methods to prepare natural nootkatone.

Several methods exist for the production of nootkatone, but each has limitations. For example, U.S. Pat. No. 5,847,226 discloses nootkatone production by oxidizing valencene to nootkatone, nootkatol or mixtures of nootkatone and nootkatol in the presence of an unsaturated fatty acid hydroperoxide. However, in the '226 patent the fatty acid hydroperoxide is generated by autooxidation, photooxidation, chemically catalyzed oxidation or by enzymatic oxidation using lipoxygenase, and then the fatty acid hydroperoxide catalyzes the autooxidation of valencene. Such an autooxidization is generally not a selective process. Previous attempts to use microbial or enzymatic transformations to prepare nootkatone have generally resulted in low yields. For example, Drawert et al. (1984) reported the biotransformation of valencene to nootkatone in cell suspension cultures but the starting level of valencene was too low to be practical. del Rio et al. (1991) studied the accumulation of nootkatone and valencene by callus cultures of Citrus spp. The level of nootkatone in nine-month old callus cultures was between 16–160 µg/100 g fresh weight. More recently, a Japanese patent disclosed biotransformation of valencene to nootkatone using a selected microbial fermentation, but the overall yield was low. In shake flask experiments with 50 ml working volume, only 2.5 mg of nootkatone was obtained from 500 mg of starting valencene (Okuda et al., 1994).

Thus, a commercially viable method to produce nootkatone utilizing laccase would be desirable.

SUMMARY OF THE INVENTION

The invention is directed to a process for producing nootkatone by reacting valencene and a composition having laccase activity, with valencene at a concentration greater than 0.1%, in the presence of an oxygen source to form valencene hydroperoxide. The hydroperoxide is degraded to form nootkatone, and the nootkatone is recovered. The hydroperoxide may be degraded by heating and/or by contacting a catalyst. Laccase may be from a microbial source, e.g., the fungi *Botrytis cinerea* 61-34 and/or *Trametes versicolor*, or from a recombinant DNA source. A mediator and/or a solvent may be added to the valencene and the composition having laccase activity. The solvent is added at a concentration that maintains laccase activity.

The invention is also directed to a process for producing nootkatone by reacting valencene and a composition having laccase activity, wherein valencene is at a concentration of greater than 0.1%, in the presence of an oxygen source to form valencene hydroperoxide, then degrading the hydroperoxide to form nootkatone, and recovering the nootkatone. The composition having laccase activity may be a solution having a concentration of valencene up to about 64% by weight. Alternatively, laccase may be immobilized and used to oxidize valencene in the absence of a solvent.

The invention is further directed to a process for making nootkatone by reacting valencene and a composition containing laccase from either or both of *Botrytis cinerea* 61-34 or *Trametes versicolor*, with the concentration of valencene greater than 0.1%, in the presence of a mediator and an oxygen source at a pH between about pH 3–7 to form valencene hydroperoxide. The valencene hydroperoxide is degraded to form nootkatone, and the nootkatone is recovered.

The invention is still further directed to a process for producing valencene hydroperoxide. Valencene and a composition having laccase activity are reacted in the presence of an oxygen source under conditions to form valencene hydroperoxide. The starting concentration of valencene is greater than 0.1%. A mediator and/or a solvent at a concentration to maintain laccase activity may be added.

The invention is additionally directed to a process for producing nootkatone by reacting valencene and immobilized laccase in the presence of an oxygen source to form valencene hydroperoxide, heating to degrade the valencene hydroperoxide to form nootkatone, and recovering the nootkatone. In this case, the concentration of valencene in the reaction may approach 100% without abolishing the laccase activity. A mediator and/or a solvent at a concentration to maintain laccase activity may be added to the valencene and the immobilized laccase.

The invention is additionally directed to a process for producing an essential oil having increased nootkatone. An essential oil containing valencene and a composition comprising laccase are reacted in the presence of an oxygen source to form a mixture of an essential oil containing nootkatone. The mixture is heated to increase the amount of nootkatone. The essential oil containing the increased nootkatone is recovered. The starting concentration of the essential oil is greater than about 0.5%. The essential oil may be orange oil, bitter orange oil, grapefruit oil, lemon oil, and/or tangerine oil. The essential oil may be fractionated, for example, to form an extract or a distillate.

An enzymatic process which can successfully produce natural nootkatone in commercially viable quantities and with relatively few byproducts is disclosed. Laccase was used to catalyze the oxidation of valencene. Laccase from Botrytis cinerea, Trametes versicolor or other microbial sources, as well as laccase purchased from commercial vendors and/or generated using recombinant techniques, could be used in either a reaction composition or in an immobilized form. The pH range is from pH 3 to pH 7, with pH 3.5 being optimum. One or more mediators and/or solvent at a concentration to maintain laccase activity could also be added. It was also found that the methods could be used to transform a series of natural flavor chemicals due to the broad substrate specificity of the enzyme.

The objectives and other advantages of this invention will be further understood with reference to the following figures, detailed description and examples.

DETAILED DESCRIPTION

The invention is directed to a commercially viable method to produce natural nootkatone using laccase. Surprisingly, we found that the enzyme laccase (benzenediol:oxidoreductase:EC 1.10.3.2) can be used to catalyze valencene oxidation to nootkatone in commercially feasible yields. Laccase, either a monomeric or multimeric copper-containing glycoprotein, is a naturally occurring lignolytic enzyme found in woody plants that synthesize lignin and in fungal species that degrade lignin.

Materials

Laccase may be obtained from a microbial source, a commercial vendor (e.g., Sigma), or may be produced by recombinant DNA techniques using methods known to one skilled in the art. An example of a microbial source of laccase is white rot fungi such as Botrytis cinerea or Trametes versicolor. Laccase from Botrytis cinerea 61-34 and Trametes versicolor in a broth was a gift from Dr. James P. Nakas at the College of Environmental Science and Forestry at the State University of New York in Syracuse. The laccase activity level was 630–1130 nkat/ml. The enzyme is stable at least for six months under refrigeration (about 4° C.).

Valencene was obtained from Givaudan Roure Flavors, Lakeland, FL with a purity of 84–85%. Valencene may also be obtained from other manufacturers, as well as by fractionation of essential oils, for example by using extraction or distillation techniques. Essential oils are defined as volatile oils, usually having the characteristic odor or flavor of the plant from which they are obtained, used to make perfumes and flavorings. Examples of essential oils include orange oil, bitter orange oil, grapefruit oil, lemon oil, tangerine oil, citrus oil, etc.

A mediator as used herein is defined as a diffusible molecule that is activated by an oxidative enzyme and diffuses from the active site on the enzyme to a susceptible structure. While laccase can function as a catalyst independently, it is known that the presence of certain mediators may enhance the laccase-catalyzed reaction. The following chemicals have been found to be active as mediators: 1-hydroxybenzotriazole (HBT), 2,2'-azino-bis(3-ethylbenzthiazoline-6-sulfonic acid (ABTS), ferulic acid, dimethyoxy benzyl alcohol, dimethamino benzoic acid, catechin, epicatechin, p-hydroxyphenylacetic acid, quercetin, chloropromazine, phenothiazine, naringin, promazine, homovanillic acid, 4-amino-salicylic acid, syringic acid, 4-hydroxycinnamic acid, 4-amino-3-hydroxybenzoic acid, vanillic acid, isovanillic acid, caffeic acid, α-resorcylic acid, β-resorcylic acid, γ-resorcylic acid, 2,3-dihydroxybenzoic acid, 3,4-dihydroxybenzoic acid, 4-hydroxybenzoic acid, 3-hydroxybenoic acid, 2,4,6-trihydroxybenzoic acid, benzoic acid, cinnamic acid, sodium benzoate and salicylic acid. Mediators used were purchased either from Sigma Chemical Co. or Aldrich Chemical Co. It will be recognized by one skilled in the art that other related chemicals might also be useful as mediators.

Procedure for Enzymatic Transformation

Valencene and a composition having laccase activity were reacted in the presence of an oxygen source. A starting concentration of valencene of at least about 0.1% was required for commercial feasibility. When the composition having laccase activity was in solution, the concentration of valencene could be up to about 64% by weight.

Alternatively an enzyme such as laccase can be immobilized or bound on a solid support, as known to one skilled in the art. Examples of immobilization techniques are found in J. Mol. Cat. B: Enzymatic 6 (1999) 29–39; Chibata et al. Biocatalysis: Immobilized cells and enzymes, J. Mol. Cat. 37(1986) 1–24; Sharma et al., Immobilized Biomaterials Techniques and Applications, Angew. Chem. Int. Ed. Engl. 21(1982) 837–854; Laskin (Ed.), Enzymes and Immobilized Cells in Biotechnology, which are expressly incorporated by reference herein in its entirety. It is generally known that an immobilized enzyme often shows increased resistance to organic solvents as compared to the enzyme in the unbound state. Thus, it can be assumed that once laccase is immobilized or stabilized by other methods such as cross-linked enzyme crystals (Altus Biologics, Inc.), higher concentrations of valencene may be used. When immobilized on a solid support, for example on a column, the concentration of valencene in the reaction mixture could approach 100%. Therefore, various changes, modifications or alternations to laccase or the reaction conditions may be made without departing from the spirit or scope of the invention.

The oxygen source may be pure oxygen or a mixture of gases containing oxygen, such as air or other gas mixtures. Optionally, one or more mediators may be included at a concentration up to about 50 mM, preferably at a concentration greater than 0.1 mM and up to about 5 mM, to enhance the reaction. Preferred mediators are HBT, ferulic acid, 4-hydroxycinnamic acid, p-hydroxyphenylacetic acid and β-resorcylic acid, with HBT especially preferred. Also, one or more solvents such as water, hexane or other hydrocarbons may be included at concentrations which maintain laccase activity, defined as conditions under which laccase is able to catalyze the reaction. These conditions include proper pH, which for laccase is in the range of about pH 3–7, optimally pH 3.5. Other reaction conditions include the use of solvents that do not denature the enzyme and a certain moisture level for the enzyme to be in the proper configuration to achieve catalysis. Unless otherwise noted, reactions were performed in 0.1 M citrate buffer (pH 3.5).

Valencene was first mixed in a reaction vessel with citrate buffer at pH 3–7. If used, a mediator and/or emulsifier was also added to the mixture. The enzyme was added and the reaction continued at room temperature. The reaction may proceed for any length of time, for example, up to one week or longer, but reacting for at least about 24 hours produced commercially viable quantities. The mixture was continuously stirred at a speed of up to about 700 rpm. In one embodiment the reaction occurred for about 48 hours at about 25° C.–30° C. and at a pH in the range of pH 3–7. Samples were taken periodically to monitor the conversion of valencene to nootkatone. The reaction was stopped by raising the pH to pH 9.0 with sodium carbonate and heating to at least about 55° C. A catalyst could also be added, either during heating or instead of heating, to facilitate degradation of the hydroperoxides. In one embodiment the catalyst is a physiologic compound such as iron or ascorbic acid. Examples of other catalysts are cobalt and copper.

The enzyme levels tested were from about 10 nkat/ml to 620 nkat/ml and the starting concentration of valencene was from about 0.1% to about 64%. Other embodiments included valencene at a concentration between about 1% to about 50%, or between about 1%–5%. For most experiments, the starting concentration was in the range of about 0.5% to 1.5%. An emulsifier such as Tween-80 or Triton X-100 may also be used at a concentration of 0.5%.

Recovery of Crude Product

The reaction was stopped by adjustment of the pH of the reaction broth to pH 9.0 with sodium carbonate. The mixture was then heated to at least about 55° C. to decompose the hydroperoxides. The heating time was dependent upon the temperature selected; for example, heating at a temperature of 80° C. occurred for 2 h. The mixture was extracted with methylene chloride (250 ml×3 times) or heptane (250 ml×6 times) for each 1000 ml reaction broth. The extracts were dried over sodium sulfate and the solvent was removed under reduced pressure.

Product Purification

The crude product was distilled under high vacuum, for example <5 mm Hg, in a Kugelrohr apparatus. The weight of the purified product from Kugelrohr distillation, and the nootkatone concentration in this product as determined from an external calibration curve, were used to calculate the overall nootkatone yield from valencene. Other methods for recovering nootkatone, such as steam distillation, chromatography and crystallization, could be used as known to one skilled in the art.

The unreacted valencene may also be recovered and recycled for use as a substrate in subsequent reactions by methods known to one skilled in the art such as silica gel chromatography, distillation, or crystallization. Recovery of the unreacted valencene for reuse adds to the commercial viability of the invention due to the expense of valencene.

Measurement of Laccase Activity

The measurement of laccase activity was based on the oxidative dimerization of 2,6-dimethoxyphenol (DMOP), as described in Slomczynski et al. 1995, which is expressly incorporated herein by reference in its entirety. Briefly, to 500 µl of 5 mM 2,6-DMOP was added 500 µl of 0.1 M citrate NaOH (pH 3.5), followed by a 10 µl aliquot of enzyme dilution. Reaction mixtures were monitored spectrophotometrically at 477 nm.

Analytical Procedure

Samples (1 ml) were periodically taken during the reaction and were extracted with 0.8 ml methylene chloride. The separated methylene chloride layer was subjected to analysis by gas chromatography. After stopping the reaction, the recovered product after Kugelrohr distillation was diluted, for example with 95% ethanol, methyltertbutyl ether (MTBE), or methylene chloride, to a 2.5% concentration before analysis by gas chromatography (GC). For analysis of valencene and nootkatone, a Supelco SPB-1 column (30 m, internal diameter (ID) 0.25 mm, film 0.25 microns) was used, with an injector temperature of 250° C. and a program temperature of 120° C.–270° C. at 10° C./min and holding for 20 min.

Figure 1:
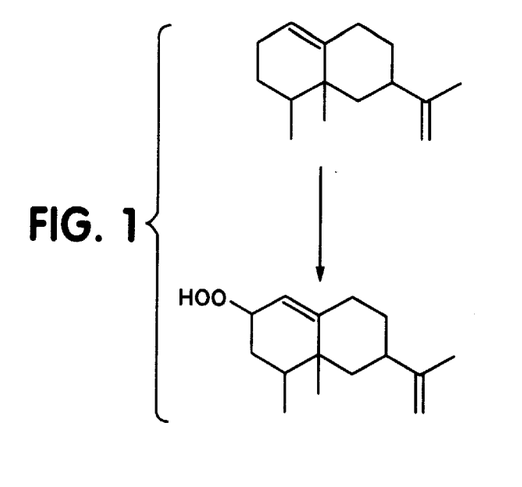
FIG. 1 shows the reaction for generation of valencene hydroperoxides.

As shown in FIG. 1, oxidation of valencene results in hydroperoxides. The hydroperoxides generated in the enzymatic process decompose in the injector port of the gas chromatograph. To characterize the formation of hydroperoxides during the enzymatic reaction, hydroperoxides were measured using either the AOAC Official Method Analysis (1997) or a thin layer chromatography (TLC) method (Johnson and Nidy, 1975). Hydroperoxides were also detected by liquid chromatography/mass spectroscopy (LC/MS) using the method of Herderich et al. (1997) and Schneider et al. (1997).

Valencene hydroperoxide was present in the reaction mixture after the enzymatic oxidation, as confirmed by nuclear magnetic resonance (NMR) analysis of a sample isolated by high performance liquid chromatography (HPLC).

Analysis of Valencene Hydroperoxide

Figure 2:
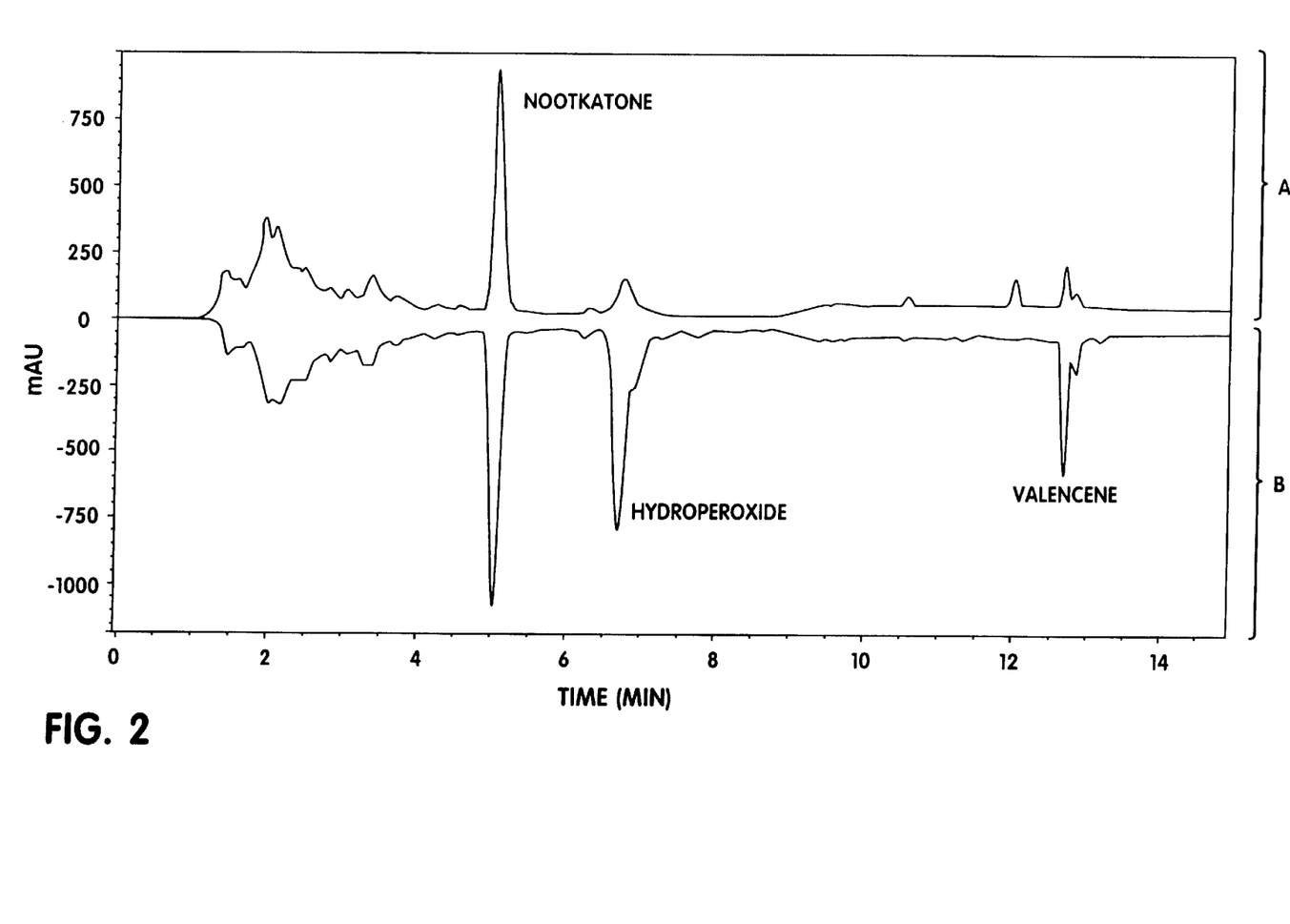
FIG. 2 is a high performance liquid chromatogram of enzymatic reaction product mixtures.
Figure 3A:
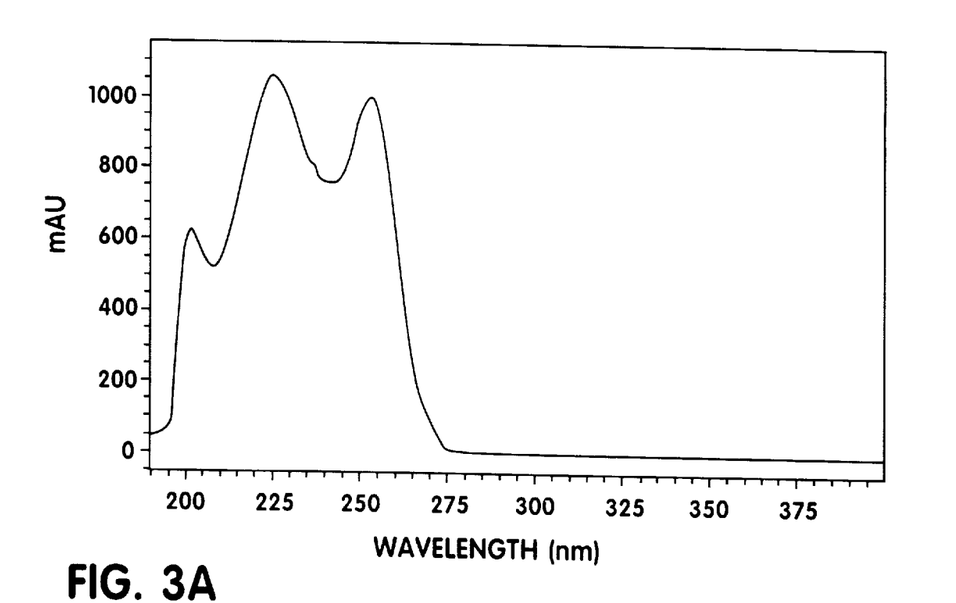
FIG. 3A is an ultraviolet spectrum of nootkatone.
Figure 3B:
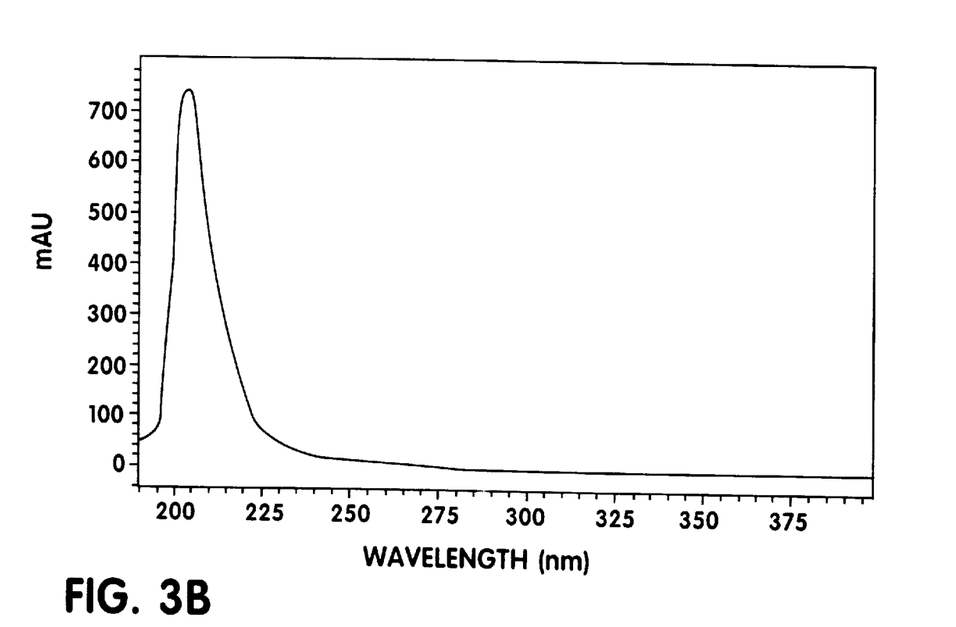
FIG. 3B is an ultraviolet spectrum of the hydroperoxide of valencene.

A high peroxide value was found in the product mixture of the enzymatic reaction, and decreased to almost zero after reflux. According to gas chromatographic (GC) analysis, however, there was no significant compositional difference before and after reflux, which was likely due to the thermal lability of the hydroperoxides. As shown in FIG. 2, HPLC analysis of the reaction mixtures revealed that one peak with a retention time of 6.7 min. disappeared after refluxing the reaction mixture. HPLC chromatograms of product mixtures of enzymatic reactions were obtained after reflux (FIG. 2A) and before reflux (FIG. 2B). A Luna C18(2), 150×2 mm, 3 µ column was used. The eluant was a gradient of methanol:water (80:20) for 4 min to 100% methanol in 1 min, at a flow rate of 0.25 ml/min. Detection was at 210 nm. Fractions corresponding to the peak were collected; these fractions clearly exhibited hydroperoxide activity based on tests with potassium iodide/starch and $FeSO_4/NH_4SCN$ solutions (AOAC 1990; Johnson and Nidy, 1975). Analysis of the ultraviolet (UV) spectrum of nootkatone (FIG. 3A) was compared with the UV spectrum of this hypothetical hydroperoxide peak (FIG. 3B). The spectrum was similar to that of valencene, but was different from that of nootkatone and lacked the enone absorptions at 230 nm and 255 nm.

Isolation of Valencene Hydroperoxides

A crude methylene chloride extract of the reaction mixture was fractionated by flash chromatography (Flash 40M, KP-Sil, 31–63 μm, 90 g). The solvent system was selected based on thin layer chromatography (TLC) experiments. The sample was eluted with methylene chloride followed with MTBE. A total of 70 fractions were collected and analyzed by TLC using thiocyanate iron(II)sulfate as the visualization reagent. Hydroperoxides oxidize Fe(II) to Fe(III), which reacted with thiocyanate to form blood red $Fe(SCN)_5^{2-}$ (Johnson and Nidy, 1975). The TLC experiments showed that fractions 7–12 were hydroperoxide active. An HPLC analysis was conducted on the combined fractions. The major component in fractions 7–12 corresponded to the HPLC peak of the hypothetical hydroperoxide. Evaporation of solvents from fractions 7–12 provided a material which was identified as valencene hydroperoxide.

Figure 4A:
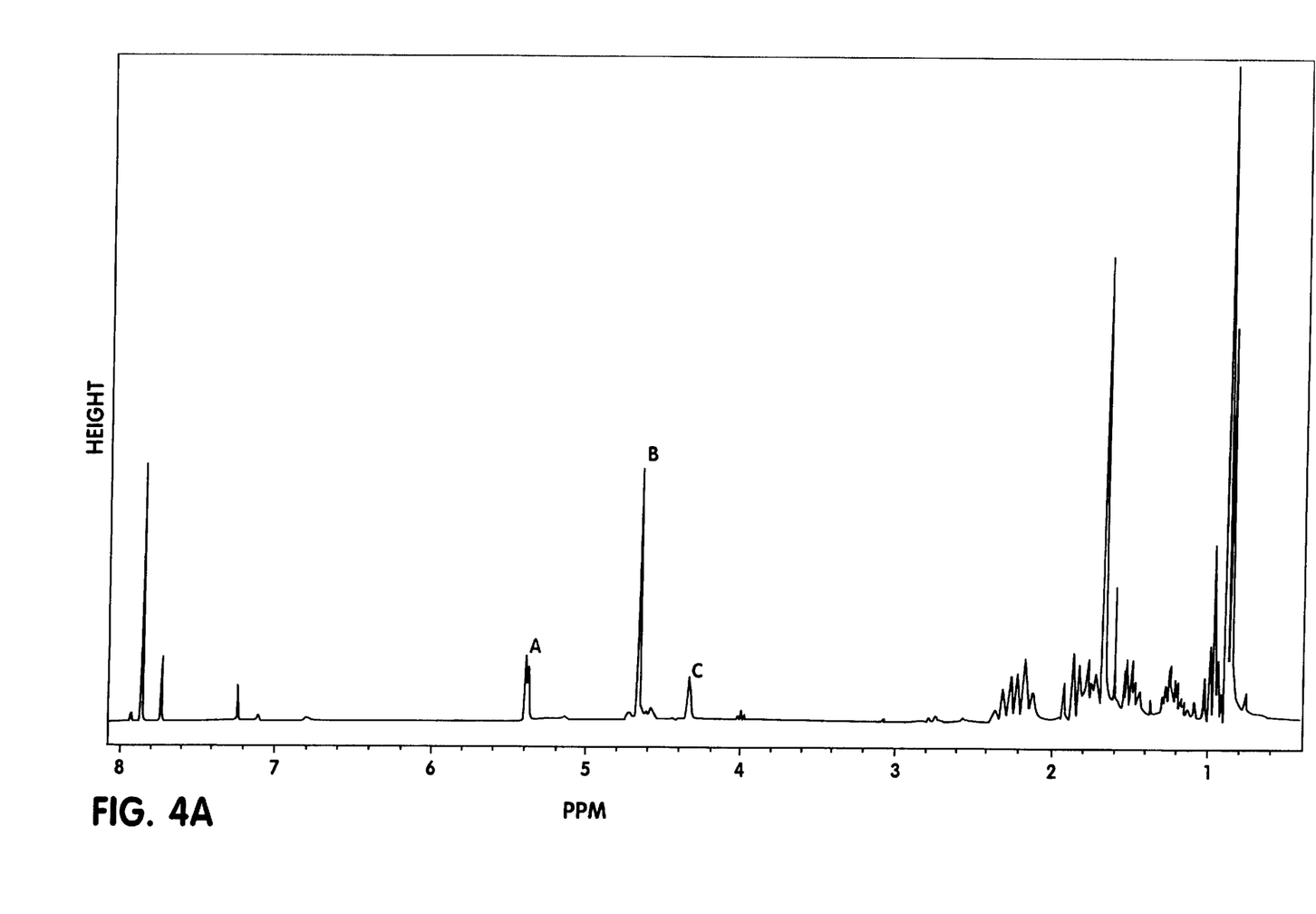
FIG. 4A is a $^1$H nuclear magnetic resonance spectrum showing valencene hydroperoxides after enzymatic oxidation.
Figure 4B:
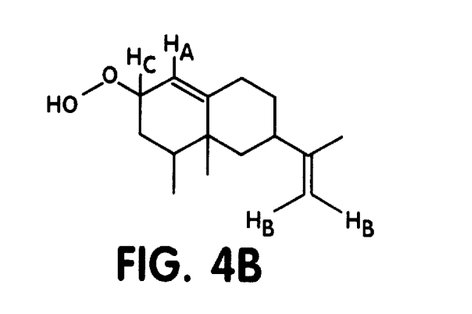
FIG. 4B is the compound profiled in FIG. 4A.
Figure 5A:
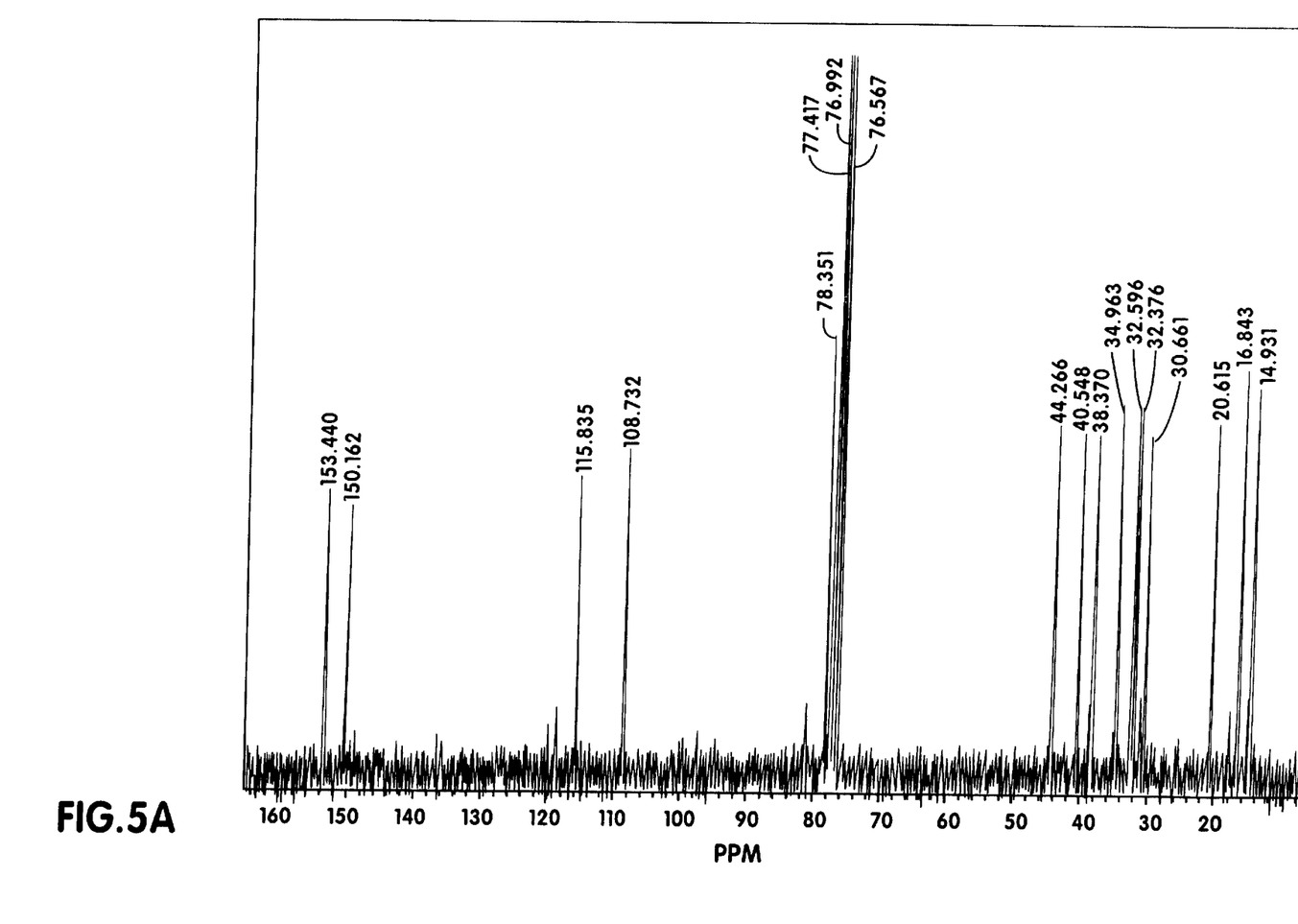
FIG. 5A is a $^{13}$C nuclear magnetic resonance spectrum showing valencene hydroperoxides after enzymatic oxidation.
Figure 5B:
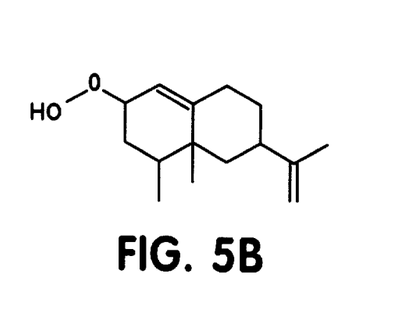
FIG. 5B is the compound profiled in FIG. 5A.
Figure 7:
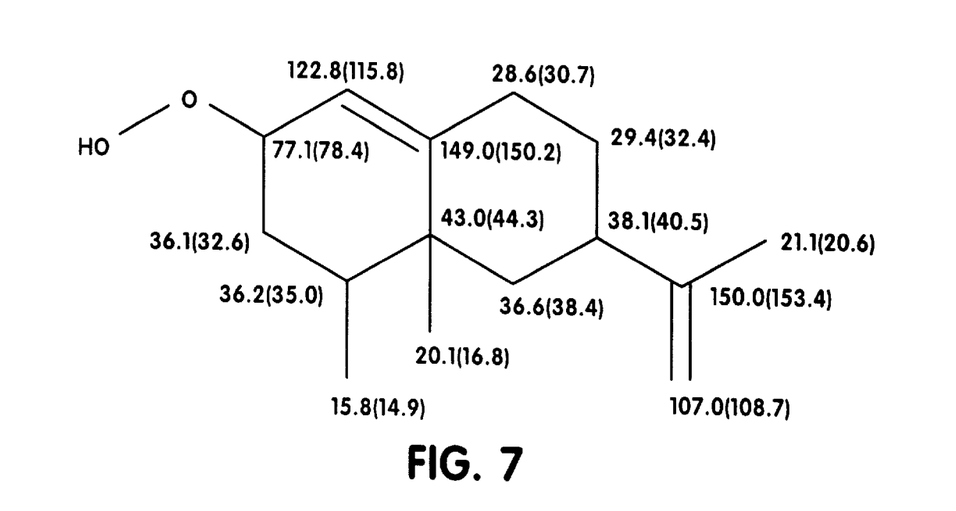
FIG. 7 is a chemical structure of valence hydroperoxide indicating the calculated and experimental (in parenthesis) $^{13}$C chemical shifts.

NMR Experiments $^1H-$, $^{13}C-$, DEPT, $^1H^1H$-correlation and $^1H^{13}C$-correlation experiments were carried out on the material from fractions 7–12. FIG. 4A shows the proton ($^1H$) nuclear magnetic resonance (NMR) spectrum of the compound shown in FIG. 4B. FIG. 5A shows the $^{13}C$ NMR spectrum of the compound shown FIG. 5B. From the chemical shifts and the multiplicities of $^{13}C$ signals, it can be seen that the carbon skeleton was very similar to that of valencene. With reference to FIG. 5A, one carbon resonance line appears at 78.4 ppm, which is typical for carbon connected to an oxygen atom. However, this carbon line is 13.9 ppm further downfield in comparison with the corresponding alcohol. The chemical shift of the proton attached to the carbon (C—O) is 4.33 ppm, whereas the corresponding proton of the alcohol has a chemical shift of 4.04 ppm. FIG. 7 corresponds to the calculated $^{13}C$ chemical shifts of valencene hydroperoxide, with experimental results in parentheses, obtained using the material from fractions 7–12. The calculated $^{13}C$ chemical shifts of valencene hydroperoxide are very close to that of the major component in the fraction group 7–12 shown in FIG. 5A. According to these experimental results, it can be concluded that the hydroperoxide in the enzymatic reaction mixture has the chemical structure shown in FIG. 7.

The invention will be further appreciated in light of the following examples.

EXAMPLE 1

The enzymatic oxidation of valencene was carried out in a 1.5 liter reaction vessel (New Brunswick Scientific). The reaction mixture consisted of 450 ml of 0.1 M citrate buffer (pH 3.5), 2.5 ml of 0.1 M HBT, 2.5 ml of Tween-80, 2.5 ml of valencene and 50 ml of Botrytis fermentation broth (laccase activity level of 110 nkat/ml). Air was used as a source of oxygen and was supplied in the manner of high-speed agitation (about 500–700 rpm). The reaction was carried out at room temperature (about 25° C.–30° C.). After two days, the reaction was stopped by changing the pH of the mixture to 9.0 with sodium carbonate and heating in a boiling water bath for two hours.

Figure 6:
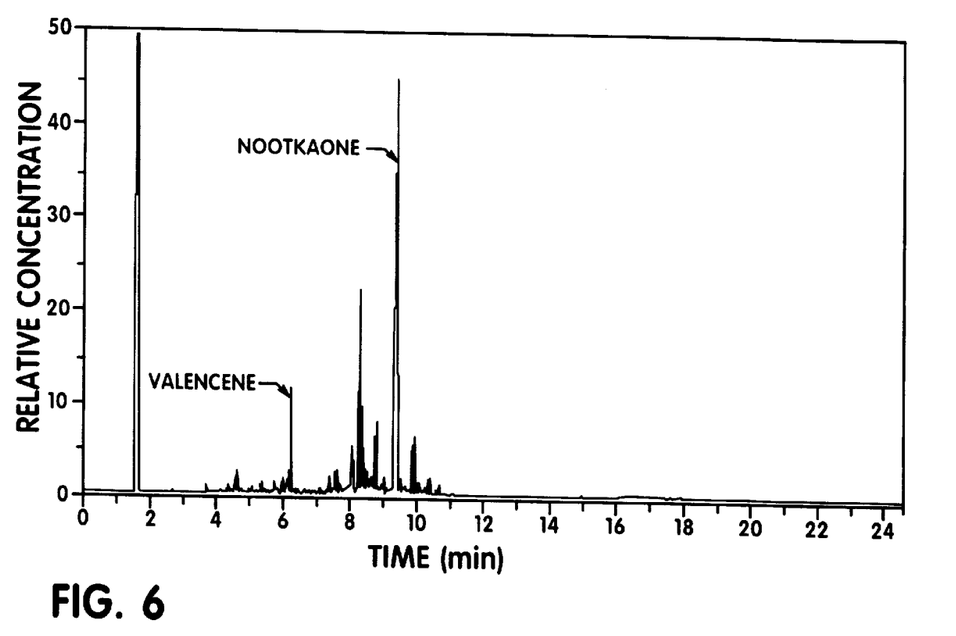
FIG. 6 is a gas chromatographic profile of an enzymatic reaction product.

After cooling to room temperature, the mixture was extracted with methylene chloride (3×150 ml each). The combined organic phases were dried over $Na_2SO_4$ and concentrated under vacuum. The crude product (3.5 ml) was distilled using a Kugelrohr apparatus and analyzed by gas chromatography (GC). With reference to FIG. 6, a typical GC profile of a 2.5% solution of the product after distillation showed that nootkatone was the largest peak and accounted for 43.3 $\%^{w/w}$, as determined from an external curve. The overall yield of nootkatone from this reaction was 28.6 $\%^{w/w}$. The unreacted valencene was 33.4 $\%^{w/w}$.

EXAMPLE 2

The enzymatic oxidation of valencene was carried out in a two liter reaction vessel. The reaction mixture consisted of 1405 ml of 0.1 M citrate buffer (pH 3.5), 30 ml of 0.1 M HBT, 30 ml of Tween-80, and 30 ml of valencene. The reaction was initiated by adding 5 ml of fermentation broth from *Trametes versicolor* (laccase activity level of 11 nkat/ml). Air was used as a source of oxygen and was supplied in the manner of agitation at 350 rpm. The reaction was carried out at a temperature of 30° C. The reaction was stopped after nine days and the product was recovered as in Example 1. The overall yield of nootkatone from this reaction was 22.38 $\%^{w/w}$. The unreacted valencene was 37.34 $\%^{w/w}$.

EXAMPLE 3

In a shake flask, a reaction mixture (20 ml) consisting of 0.1 M citrate buffer (pH 3.5), HBT mediator (0.5–16 mM final concentration), Tween-80 (0.5%), valencene (0.5–64%) and laccase (activity level of 60 nkat/ml) were incubated at 30° C. with shaking at 225 rpm for 48 hours. When the reaction was stopped, a 2 ml sample was taken from each flask and extracted with 1.2 ml of methylene chloride. The separated solvent layer was analyzed by GC. The area percentage corresponding to valencene and nootkatone are listed below.

| Starting valencene level (%) | Valencene (area %) | Nootkatone (area %) |
|---|---|---|
| 0.5 | 32.10 | 17.09 |
| 1 | 32.97 | 15.70 |
| 2 | 41.89 | 9.41 |
| 4 | 57.97 | 4.25 |
| 8 | 68.42 | 2.47 |
| 16 | 81.02 | 0.85 |
| 32 | 82.12 | 0.33 |
| 48 | 83.92 | 0.03 |
| 64 | 84.35 | 0.02 |
| 64 (before adding laccase) | 91.12 | 0.004 |

EXAMPLE 4

The conversion of valencene to nootkatone in the presence and absence of laccase and/or a mediator was evaluated. The total reaction volume in each flask was 10 ml. Laccase was from *Botrytis cinerea* at an activity level of 60 nkat/ml. The mediator was HBT at a final concentration of 0.5 mM. The starting substrate (valencene) was at 0.5%. After four days, the reaction mixtures were extracted with methylene chloride and the separated organic phases were analyzed by GC. The results are shown below.

| Laccase | Mediator | Valencene (area %) | Nootkatone (area %) |
|---|---|---|---|
| + | + | 40.45 | 43.79 |
| + | − | 72.86 | 10.80 |
| − | + | 85.50 | 2.96 |

EXAMPLE 5

In the total reaction volume of 10 ml, consisting of laccase at a level of 620 nkat/ml, 0.5% of valencene as the substrate and 0.5% of Tween-80, the following compounds at a concentration of 0.5 mM were tested as mediators: 1-hydroxybenzotriazole (HBT), 2,2'-azino-bis (3-ethylbenzthiazoline-6-sulfonic acid (ABTS), ferulic acid (FA), dimethyoxy benzyl alcohol (DBA) and dimethamino benzoic acid (DBAD). The following table indicates the relative amount of valencene and nootkatone after four days of reaction in the presence of various mediators.

| Mediator | Valencene (area %) | Nootkatone (area %) |
| --- | --- | --- |
| HBT | 18.17 | 58.28 |
| ABTS | 75.49 | 14.43 |
| FA | 59.54 | 17.21 |
| DBA | 68.53 | 15.92 |
| DBAD | 65.25 | 15.48 |

EXAMPLE 6

In a reaction volume of 20 ml consisting of laccase at 60 nkat/ml, 1% of valencene as the substrate and 1% of Tween-80, the following compounds were tested at a concentration of 5 mM as the mediators: catechin, epicatechin, p-hydroxyphenylacetic acid, quercetin, chloropromazine, phenothiazine, naringin, promazine, homovanillic acid, 4-amino-salicylic acid, syringic acid, 4-amino-3-hydroxybenzoic acid, vanillic acid, caffeic acid, protocatechuic acid, α-resorcylic acid, β-resorcylic acid, γ-resorcylic acid, 2,3-dihydroxybenzoic acid, 4-hydroxybenzoic acid, 3-hydroxybenzoic acid, 2,4,6-trihydroxybenzoic acid, benzoic acid, cinnamic acid, isovanillic acid, sodium benzoate and salicylic acid. In each case, the conversion rate was two to eight times greater than that observed in the absence of a mediator, which indicates that these compounds function as mediators in the process.

EXAMPLE 7

The reaction mixture at a volume of 10 ml, consisting of laccase from *Botrytis cinerea* at a level of 60 nkat/ml, 0.5% of valencene as the substrate, 0.5% of Tween-80, HBT as the mediator at a final concentration of 0.5 mM, and buffers (0.1 M) to adjust the pH, was incubated at 30° C. with shaking at 225 rpm. After six days of reaction, 2 ml samples were taken from each flask and extracted with methylene chloride before GC analysis. The following table lists the results under different pH conditions.

| pH | Valencene (area %) | Nootkatone (area %) |
| --- | --- | --- |
| 3.5 | 17.90 | 59.13 |
| 5.0 | 16.35 | 52.81 |
| 7.0 | 72.02 | 5.03 |

EXAMPLE 8

The enzymatic oxidation of orange oil containing valencene was carried out in a 1.5 liter vessel. The reaction broth, consisting of 875 ml of 0.1 M citrate buffer (pH 3.5), 5 ml of Tween-80, 5 ml of 0.1 M HBT, 5 ml of orange oil and 100 ml laccase broth from *Botrytis cinerea* (at an activity level of 63 nkat/ml), was incubated at 30° C. with agitation of 500 rpm. After four days, the product after Kugelrohr distillation was recovered following the procedure as detailed in Example 1. Analysis by GC/MS confirmed the presence of nootkatone in the product.

Organoleptic testing of both orange oils before and after oxidation was performed by nine trained flavorists using the following compositions:

| Compound | Mixture A | Mixture B |
| --- | --- | --- |
| sucrose | 10% | 10% |
| citric acid | 0.15% | 0.15% |
| orange oil (before oxidation) | 10 ppm | — |
| orange oil (after oxidation) | — | 10 ppm |

All of the flavorists could distinguish mixture A from mixture B. The flavorists described the flavor of mixture B as longer lasting with fruity, nootkatone-like flavor and strong woody notes.

It should be understood that the embodiments of the present invention shown and described in the specification are only embodiments of the inventors who are skilled in the art and are not limiting in any way. For example, the enzyme bound to a solid support may increase the stability of the enzyme and its tolerance to organic solvents. As another example, a large variety of chemicals can function as mediators. As still another example, oxidation of other substrates such as caryophyllene, phenylpyruvic acid, guaiene, anethole, farnesol and hop oil by laccase may be included to produce flavors. Therefore, various changes, modifications or alterations to these embodiments may be made or resorted to without departing from the spirit of the invention and the scope of the following claims.

What is claimed is:

1. A process for producing nootkatone comprising:
   (a) reacting valencene and a composition having laccase activity, wherein valencene is at a concentration of greater than 0.1%, in the presence of an oxygen source to form valencene hydroperoxide,
   (b) degrading the hydroperoxide to form nootkatone, and
   (c) recovering nootkatone.
2. The process of claim 1 wherein the hydroperoxide is degraded by heating.
3. The process of claim 1 wherein the hydroperoxide is degraded by a catalyst.
4. The process of claim 3 wherein the catalyst is selected from the group consisting of iron, ascorbic acid, cobalt, copper and combinations thereof.
5. The process of claim 1 wherein laccase is from a microbial source.
6. The process of claim 5 wherein the microbial source is a fungus that degrades wood.
7. The process of claim 6 wherein the microbial source is a white rot fungi selected from the group consisting of *Botrytis cinerea, Trametes versicolor* and combinations thereof.
8. The process of claim 1 wherein the laccase is from a recombinant DNA.
9. The process of claim 1 further comprising adding a mediator to the valencene and the composition having laccase activity.
10. The process of claim 9 wherein the mediator is selected from the group consisting of 1-hydroxybenzotriazole, 2,2'-azino-bis(3-ethylbenzthiazoline-6-sulfonic acid), ferulic acid, dimethoxy benzyl alcohol, dimethylamino benzoic acid, catechin, epicatechin, p-hydroxyphenylacetic acid, quercetin, chloropromazine, phenothiazine, naringin, promazine, homovanillic acid, 4-amino-salicylic acid, syringic acid, 4-hydroxycinnamic acid, 4-amino-3-hydroxybenzoic acid, vanillic acid, isovanilic acid, caffeic acid, α-resorcylic acid, β-resorcylic acid, γ-resorcylic acid, 2,3-dihydroxybenzoic acid, 3,4-dihydroxybenzoic acid, 4-hydroxybenzoic acid, 3-hydroxybenoic acid, 2,4,6-trihydroxybenzoic acid, benzoic acid, cinnamic acid, sodium benzoate and salicylic acid and combinations thereof.

11. The process of claim 9 wherein the mediator is at a concentration greater than about 0.1 mM and up to about 50 mM.

12. The process of claim 1 wherein the oxygen source is selected from the group consisting of an oxygen containing gas mixture and pure oxygen.

13. The process of claim 1 wherein the valencene and the composition having laccase activity are reacted for at least about 24 hours prior to heating to form the valencene hydroperoxide.

14. The process of claim 1 wherein the heating is to a temperature of at least about 55° C.

15. The process of claim 1 further comprising adding a solvent at a concentration to maintain laccase activity to the valencene and the composition having laccase activity.

16. The process of claim 1 wherein the composition is a solution and the concentration of valencene is up to about 64% by weight.

17. The process of claim 1 wherein the laccase is immobilized.

18. A process for making nootkatone comprising:
  (a) reacting valencene and a composition comprising laccase selected from the group consisting of *Botrytis cinerea* 61-34, *Trametes versicolor* and combinations thereof, wherein the concentration of valencene is greater than 0.1%, in the presence of a mediator and an oxygen source at a pH between about 3–7 to form valencene hydroperoxide,
  (b) degrading the valencene hydroperoxide to form nootkatone, and
  (c) recovering nootkatone.

19. The process of claim 18 wherein the degrading is by heating to at least about 55° C.

20. The process of claim 18 further comprising adding a catalyst to step (b).

21. The process of claim 20 wherein the catalyst is selected from the group consisting of iron, ascorbic acid, cobalt, copper and combinations thereof.

22. The process of claim 18 wherein the oxygen source is selected from the group consisting of a mixture of gases containing oxygen and pure oxygen.

23. The process of claim 19 wherein the reaction proceeds for at least about 24 hours.

24. The process of claim 18 wherein the mediator is selected from the group consisting of 1-hydroxybenzotriazole, ferulic acid, 4-hydroxbenzotriazole acid, β-resorcylic acid and combinations thereof.

25. The process of claim 18 wherein the mediator is at a concentration greater than about 0.1 mM and up to about 5 mM.

26. A process for producing valencene hydroperoxide comprising reacting valencene, a composition having laccase activity and an oxygen source under conditions to form said valencene hydroperoxide.

27. The process of claim 26 wherein the starting concentration of valencene is greater than 0.1%.

28. The process of claim 26 further comprising adding a mediator.

29. The process of claim 26 further comprising adding a solvent at a concentration that maintains laccase activity.

30. A process for producing nootkatone comprising
  (a) reacting valencene and an immobilized laccase in the presence of an oxygen source to form valencene hydroperoxide,
  (b) heating to degrade the valencene hydroperoxide to form nootkatone, and
  (c) recovering nootkatone.

31. The process of claim 30 wherein valencene is at a concentration of about 86%.

32. The process of claim 30 further comprising adding a mediator to the valencene and the immobilized laccase.

33. The process of claim 30 further comprising adding a solvent at a concentration to maintain laccase activity to the valencene and the immobilized laccase.

34. A process for producing an essential oil having increased nootkatone content comprising
  (a) reacting an essential oil containing valencene and a composition comprising laccase in the presence of an oxygen source to form a mixture of the essential oil containing nootkatone,
  (b) heating the mixture to increase the amount of nootkatone, and
  (c) recovering the essential oil containing the increased nootkatone.

35. The process of claim 34 wherein the starting concentration of the essential oil is greater than about 0.5%.

36. The process of claim 34 wherein the essential oil is selected from the group consisting of orange oil, bitter orange oil, grapefruit oil, lemon oil, tangerine oil and combinations thereof.

37. The process of claim 34 wherein a fraction of essential oil is reacted.

38. The process of claim 36 wherein the essential oil fraction is selected from the group consisting of an extract and a distillate.

* * * * *

UNITED STATES PATENT AND TRADEMARK OFFICE
CERTIFICATE OF CORRECTION

PATENT NO. : 6,200,786 B1
DATED : March 13, 2001
INVENTOR(S) : Rongmin Huang et al.

It is certified that error appears in the above-identified patent and that said Letters Patent is hereby corrected as shown below:

Column 1,
Line 57, "Citrus spp" should be -- *Citrus* spp --

Column 6,
Line 14, "methyltertbutyl" should be -- methyl*tert*butyl --

Column 12, claim 24,
Lines 1 and 2, "4-hydroxybenzotriazole acid" should be -- 4-hydroxycinnamic acid --

Signed and Sealed this

Fifth Day of March, 2002

*Attest:*

JAMES E. ROGAN
*Director of the United States Patent and Trademark Office*

*Attesting Officer*